United States Patent
Johnson et al.

(10) Patent No.: US 6,729,838 B2
(45) Date of Patent: May 4, 2004

(54) AUTOMATED BARREL PANEL TRANSFER AND PROCESSING SYSTEM

(75) Inventors: John A. Johnson, Littleton, CO (US); Richard K. Hansen, Morrison, CO (US); Brent K. Christner, Littleton, CO (US)

(73) Assignee: Lockheed Martin Corporation, Bethesda, MD (US)

(*) Notice: Subject to any disclaimer, the term of this patent is extended or adjusted under 35 U.S.C. 154(b) by 0 days.

(21) Appl. No.: 10/260,261

(22) Filed: Sep. 30, 2002

(65) Prior Publication Data

US 2003/0049117 A1 Mar. 13, 2003

Related U.S. Application Data

(63) Continuation of application No. 09/376,765, filed on Aug. 17, 1999, now Pat. No. 6,457,932.
(60) Provisional application No. 60/096,848, filed on Aug. 18, 1998.

(51) Int. Cl.[7] .............................................. B65G 67/02
(52) U.S. Cl. ............ 414/809; 414/331.09; 414/331.17; 414/782; 414/816
(58) Field of Search ................... 414/331.06, 331.09, 414/331.13, 331.14, 331.17, 782, 796.4, 809, 816

(56) References Cited

U.S. PATENT DOCUMENTS

| | | | |
|---|---|---|---|
| 1,999,596 A | 4/1935 | Roemer | 198/107 |
| 2,231,014 A | 2/1941 | Lytle et al. | 29/33 |
| 3,137,936 A | 6/1964 | Tomkins | 29/475 |
| 3,300,837 A | 1/1967 | Fisher et al. | 228/172 |
| 3,400,449 A | 9/1968 | Maguire et al. | 228/150 |
| 3,705,679 A | 12/1972 | Tenpas | 228/49 |
| 3,872,815 A | 3/1975 | Kawai et al. | 114/65 R |
| 3,937,316 A | 2/1976 | Gerhardt | 198/156 |
| 3,946,933 A | 3/1976 | Bergling | 228/212 |
| 4,038,786 A | 8/1977 | Fong | 51/320 |
| 4,117,939 A | 10/1978 | Haddock | 414/11 |
| 4,244,482 A | 1/1981 | Baumgart et al. | 220/3 |
| 4,392,604 A | 7/1983 | Sears | 228/212 |
| 4,442,335 A | 4/1984 | Rossi | 219/79 |
| 4,461,124 A | 7/1984 | Anderson | 51/165 R |
| 4,490,833 A | 12/1984 | Inomata et al. | 378/58 |
| 4,693,358 A | 9/1987 | Kondo et al. | 198/339.1 |
| 4,697,974 A * | 10/1987 | Eltoukhy | 414/331.09 |
| 4,721,241 A | 1/1988 | Yuasa et al. | 228/5.7 |
| 4,774,757 A | 10/1988 | Sakamoto et al. | 29/702 |
| 4,856,698 A | 8/1989 | Marianne et al. | 228/4.1 |
| 4,924,996 A | 5/1990 | Svensson et al. | 198/341 |
| 5,098,005 A | 3/1992 | Jack | 228/4.1 |
| 5,123,808 A * | 6/1992 | Fath | 414/796.4 |
| 5,130,511 A | 7/1992 | Kumagai et al. | 219/117.1 |
| 5,178,255 A | 1/1993 | Carlson | 198/346.1 |

(List continued on next page.)

Primary Examiner—Janice L. Krizek
(74) Attorney, Agent, or Firm—Marsh Fischmann & Breyfogle LLP

(57) ABSTRACT

An automated system for preparing weld land areas of panels to be welded to each other is disclosed. Generally, the system of the present invention includes a system for cleaning contaminants from such weld land areas. In one embodiment, the system for cleaning contaminants includes a system for blasting carbon dioxide granules or pellets against the weld land areas. In instances where the panels comprise aluminum, the system may further include a system for removing at least a first layer of aluminum oxide from the weld land areas. In one embodiment, the system for removing includes a system for moving a plurality of sheets of sand paper over the weld land areas. For purposes of moving the panels relative to the system for cleaning contaminants and/or the system for removing at least the first layer of aluminum oxide, the automated system of the present invention may further include a shuttle system for supporting and moving at least the first panel therethrough.

23 Claims, 20 Drawing Sheets

U.S. PATENT DOCUMENTS

| | | | |
|---|---|---|---|
| 5,203,814 A | 4/1993 | Kushizaki et al. | 29/897.2 |
| 5,313,903 A | 5/1994 | Goldbach et al. | 114/65 R |
| 5,400,943 A | 3/1995 | Rossi | 228/6.1 |
| 5,512,123 A | 4/1996 | Cates et al. | 156/272.6 |
| 5,518,166 A | 5/1996 | Numata et al. | 228/182 |
| 5,525,093 A | 6/1996 | Palmer, Jr. | 451/40 |
| 5,528,818 A | 6/1996 | Warneke | 29/564.7 |
| 5,561,527 A | 10/1996 | Krone-Schmidt et al. | 356/414 |
| 5,593,499 A | 1/1997 | Stans et al. | 118/63 |
| 5,634,255 A | 6/1997 | Bishop | 29/430 |
| 5,662,264 A | 9/1997 | Gustafsson et al. | 228/170 |
| 5,724,712 A | 3/1998 | Bishop | 29/430 |
| 6,213,849 B1 | 4/2001 | Johnson et al. | 451/75 |
| 6,457,932 B1 | 10/2002 | Johnson et al. | 414/782 |
| 2002/0090290 A1 * | 7/2002 | Spatafora et al. | 414/796.4 |

* cited by examiner

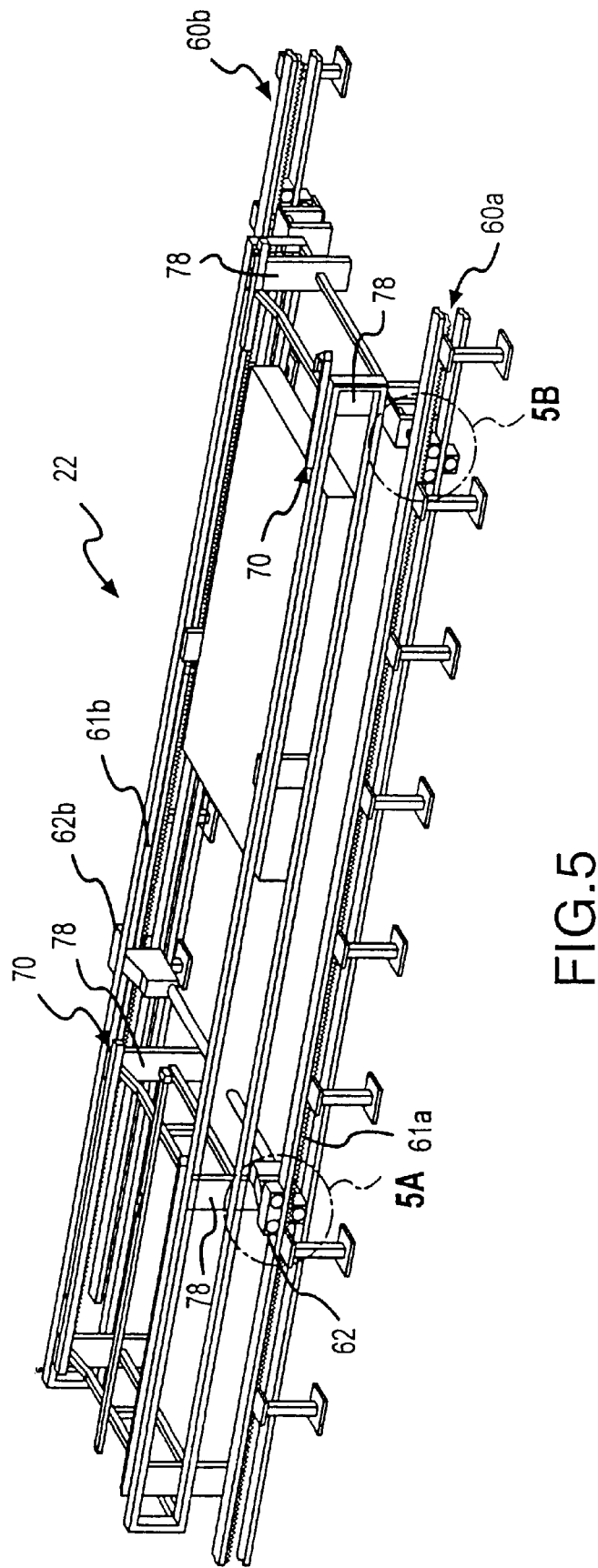

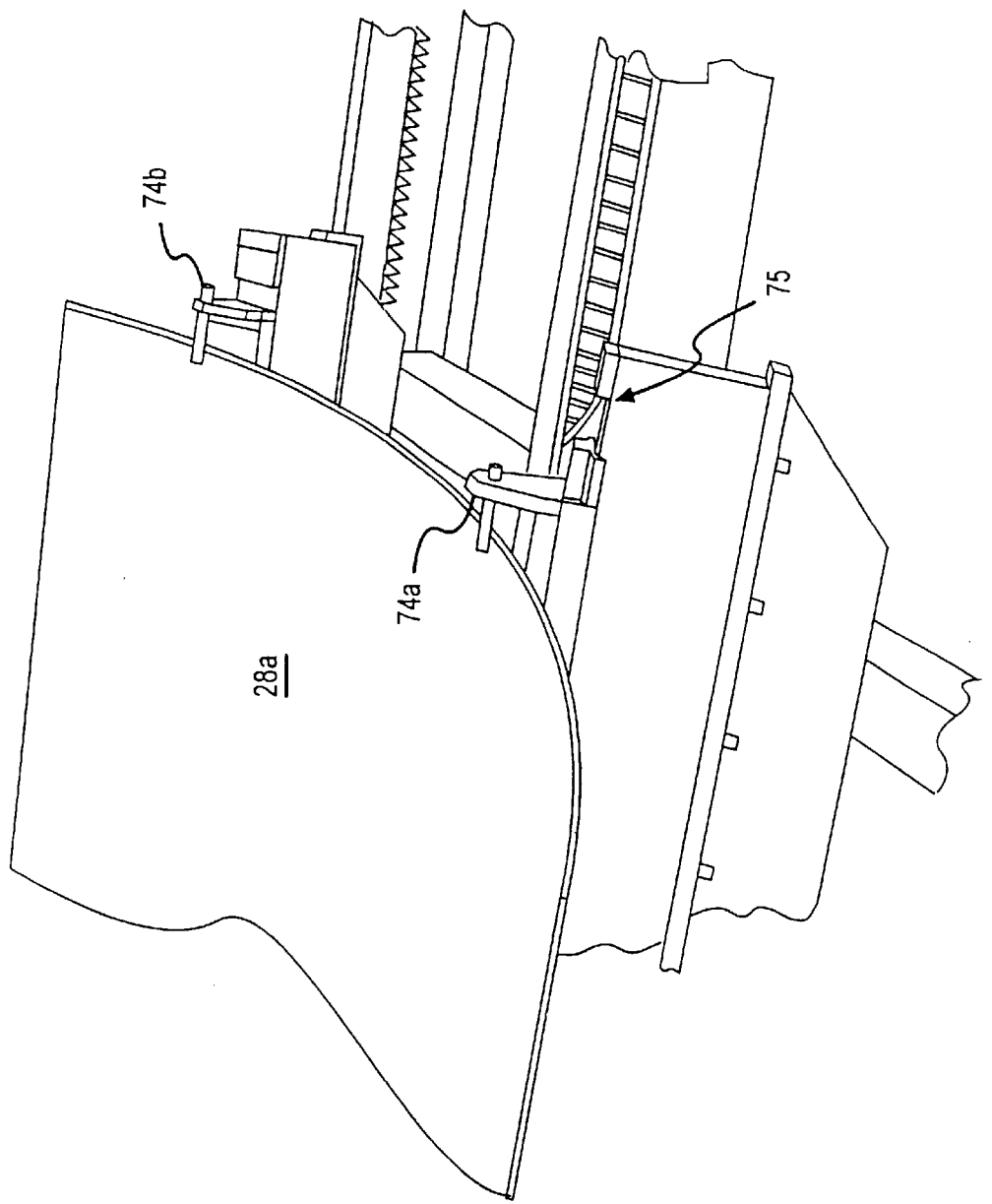

AUTOMATED BARREL PANEL TRANSFER AND PROCESSING SYSTEM

RELATED APPLICATION

This application claims priority from and is a continuation of U.S. patent application Ser. No. 09/376,765, filed on Aug. 17, 1999 (now U.S. Pat. No. 6,457,932, which issued on Oct. 1, 2002), the entire disclosure of which is incorporated by reference herein, and further claims priority U.S. Provisional Patent Application Ser. No. 60/096,848, filed on Aug. 18, 1998, the entire disclosure of which is incorporated by reference herein.

FIELD OF THE INVENTION

The present invention generally relates to a system for supporting and transferring at least a first panel from a first location to a second location, and in particular, to a system for supporting a first panel and for transporting the first panel through a panel processing system.

BACKGROUND OF THE INVENTION

Aluminum barrels (e.g., cylinders) are weldable to domes (e.g., hemispheres) to make launch vehicle propulsion (e.g., propellant or fuel) tanks. Such barrels may be made from four 90° curved panels that are weldable together along longitudinally extending seams in a vertical weld fixture or tool. Generally, for purposes of welding the panels to form a tank, the panels may be placed on a horizontal turntable of the vertical weld fixture and then rotated into clamping bars of the vertical weld fixture. Thereafter, a two torch-single pass/variable polarity gas tungsten arc system may be used to butt-weld the panels together. For a four panel fuel tank, this process is repeated four times to produce a complete barrel.

Prior to butt-welding a first panel to a second panel, the panels are typically transported from a loading area to one or more preparation areas, manually prepared (e.g., cleaned and sanded by hand) at the preparation area(s) in order to enhance the weld, and additionally moved from such panel preparation areas to the weld fixture. Current practices for both manually preparing and moving panels can be labor intensive, time consuming, expensive and inefficient.

SUMMARY OF THE INVENTION

In one aspect, the present invention is directed to an automated panel transfer and processing system. More specifically, the system of the present invention is capable of queuing, handling and processing a plurality of aluminum alloy panels (e.g., four panels) which are to be welded together to form a cylindrical portion of a propulsion (e.g., fuel or propellant) tank for use in launch vehicles. In this regard, the system of the present invention is capable of queuing and transporting at least a first panel through at least a first weld preparation station which functions to (1) clean inner and outer edge wall portions (e.g., weld lands) of at least the first panel and to (2) remove a layer comprising aluminum oxide therefrom. Thereafter, the system functions to transport at least the first panel into a weld fixture, where the side edge wall of the first panel may be trimmed (e.g., routed) and then butt-welded to another panel (e.g., a second panel) which has been transferred and processed by the system of the present invention. This system reduces costs and risks associated with manual handling and manual weld land preparation processing. In this regard, panel handling and weld land processing are now controlled and repeatable processes. The successful automation of this process in accordance with the system of the present invention reduces cycle time substantially while also reducing total labor costs and avoids extra costs by reducing the possibility of rework and risk of damage.

In another aspect, the present invention is directed to a digital radiographic weld inspection system for use on the weld fixture. As noted hereinabove, the weld fixture is vertically oriented, and includes a router for trimming side edge walls of at least the first panel to remove aluminum oxide therefrom, and a two torch-single pass/variable polarity gas tungsten arc system for butt-welding the first panel to a second panel processed in accordance with the present invention. Of importance, the vertical weld fixture further includes the digital radiographic weld inspection system. The weld inspection system, which is mountable onto the weld fixture, such that the weld inspection system can inspect welds upon completion of butt-welding operations, includes a fiber optic scintillator (FOS) x-ray to light conversion screen coupled to a high resolution charged coupled device (CCD) camera to produce radiographic images of a weld area between welded panels of the cylindrical fuel tank (e.g., first and second panels). This non-film system allows images of the weld to be viewed immediately upon acquisition on a CRT monitor and eliminates development of film, which results in simplified image review, storage and retrieval of radiographic records. As such, the system provides very fast image acquisition and electronic image enhancements not available with conventional film techniques. Moreover, the barrel welds can be radiographically inspected immediately upon completion of the weld while the panels (e.g., first and second panels) are still clamped in the weld fixture (e.g., full length weld inspection results within 75 minutes of weld completion). This allows improvements in the weld process, with attendant reduction of weld defects and weld repairs since each weld (e.g., weld connecting first and second panels) may be inspected prior to proceeding with the next weld (e.g., weld connecting second and third panels). Accordingly, weld parameters may be adjusted prior to starting another weld, thereby eliminating recurring weld problems. Additional benefits include reduced build cycle-time for assembling a launch vehicle propulsion (e.g., fuel or propellant) tank and reduced labor costs associated with re-installing a barrel into the weld fixture for a full length weld repair if required.

BRIEF DESCRIPTION OF THE DRAWINGS

FIG. 5 is a perspective view of a panel position shuttle system illustrated in FIG. 1;

FIG. 9A is an enlarged view of the circled area indicated in FIG. 9;

DETAILED DESCRIPTION

Functionally, the panel transfer and processing system of the present invention is capable of acquiring, transporting, processing and locating a range of panels vertically into a weld fixture. In the one embodiment, the panel transfer system is capable of processing four 90° segments having a 10 foot to 13 foot diameter and, in another embodiment, processing five 72° segments having a diameter of 13 feet to 14 feet. Each segment can range from 2 feet to 30 feet in length with a maximum weight of 1,000 pounds.

Figure 1:
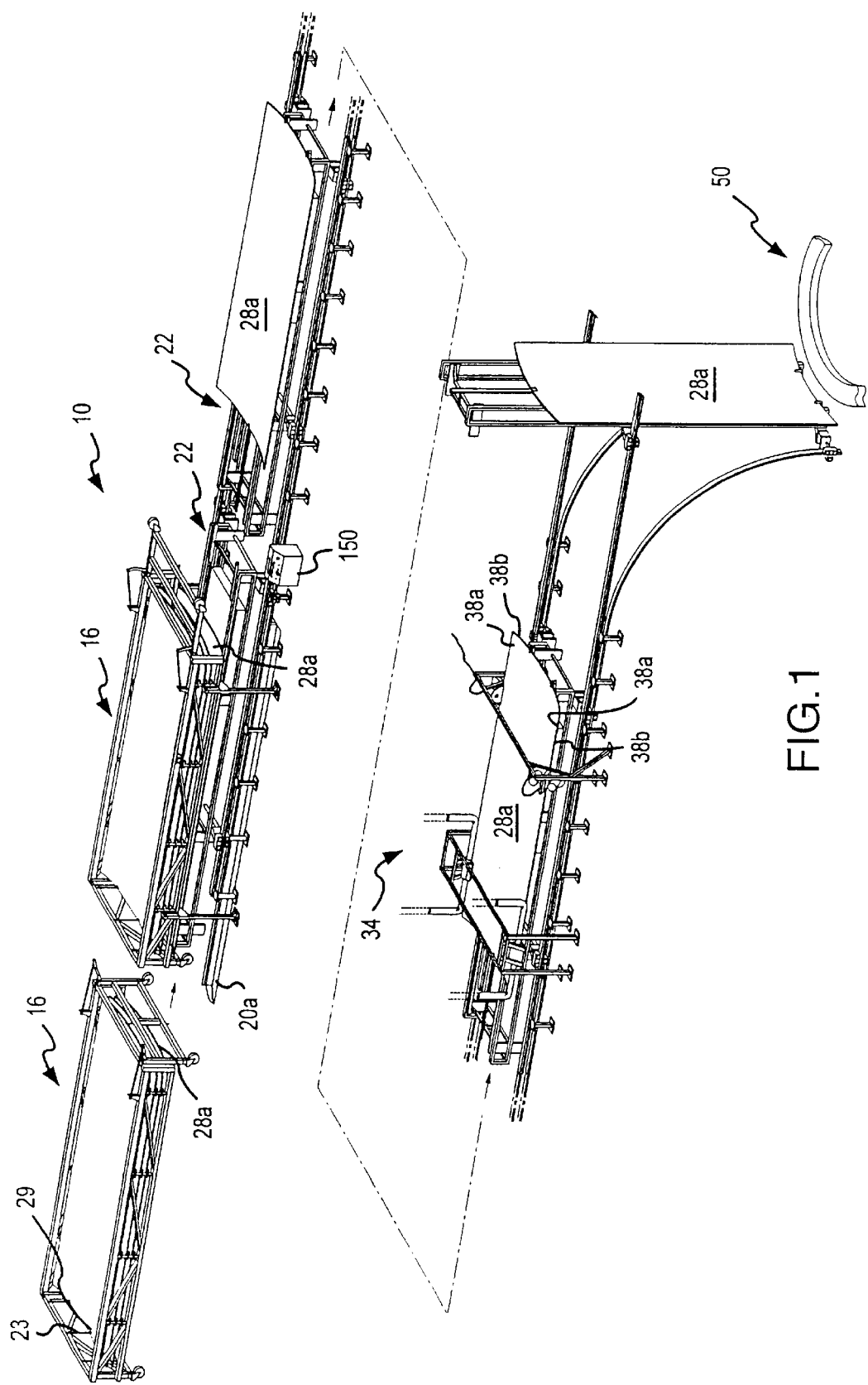
FIG. 1 is a perspective view of a first panel being transported and processed in stages by the system of the present invention.

Referring to FIG. 1, the panel transfer system 10 of the present invention includes the following major components: a panel transportation cart 16 for moving and supporting a plurality of panels from a first location to a second location, a panel position shuttle 22 for extracting at least one panel from the panel transportation cart 16 at the second location and for transporting at least a first panel 28a through the system 10, and a weld preparation station 34 for cleaning inner and outer edge wall portions of 38a, 38b of at least the first panel 28a The system 10 further includes a rail system 44 which interfaces with the panel position shuttle 22 to transport at least the first panel 28a from beneath the panel transportation cart 16, through the weld preparation station 34 and to the vertical weld fixture 50. In addition, for purposes of automating the transport and processing of the panels 28a–28d, the system 10 also includes at least a first control station 150.

Figure 2:
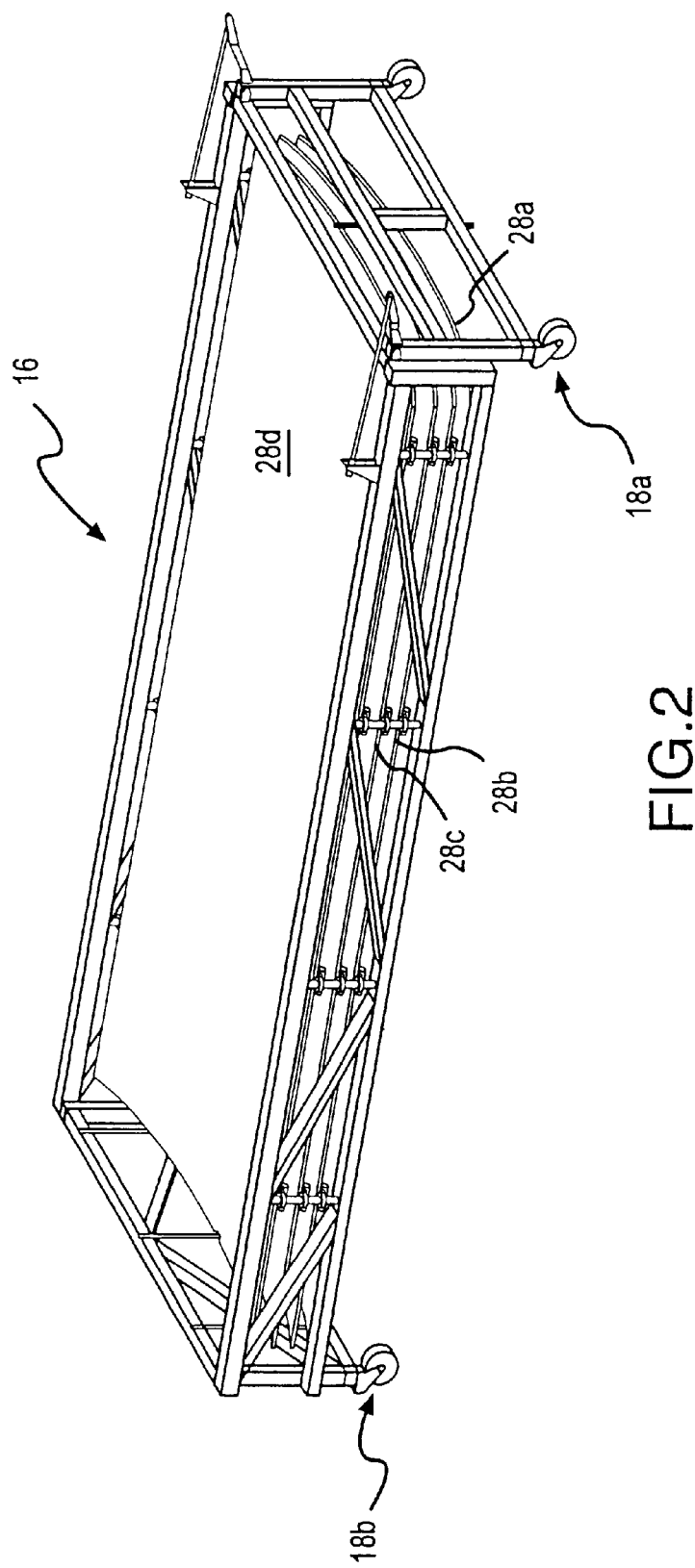
FIG. 2 is a perspective view of a plurality of panels supported by a panel transportation cart of the system illustrated in FIG. 1.
Figure 3:
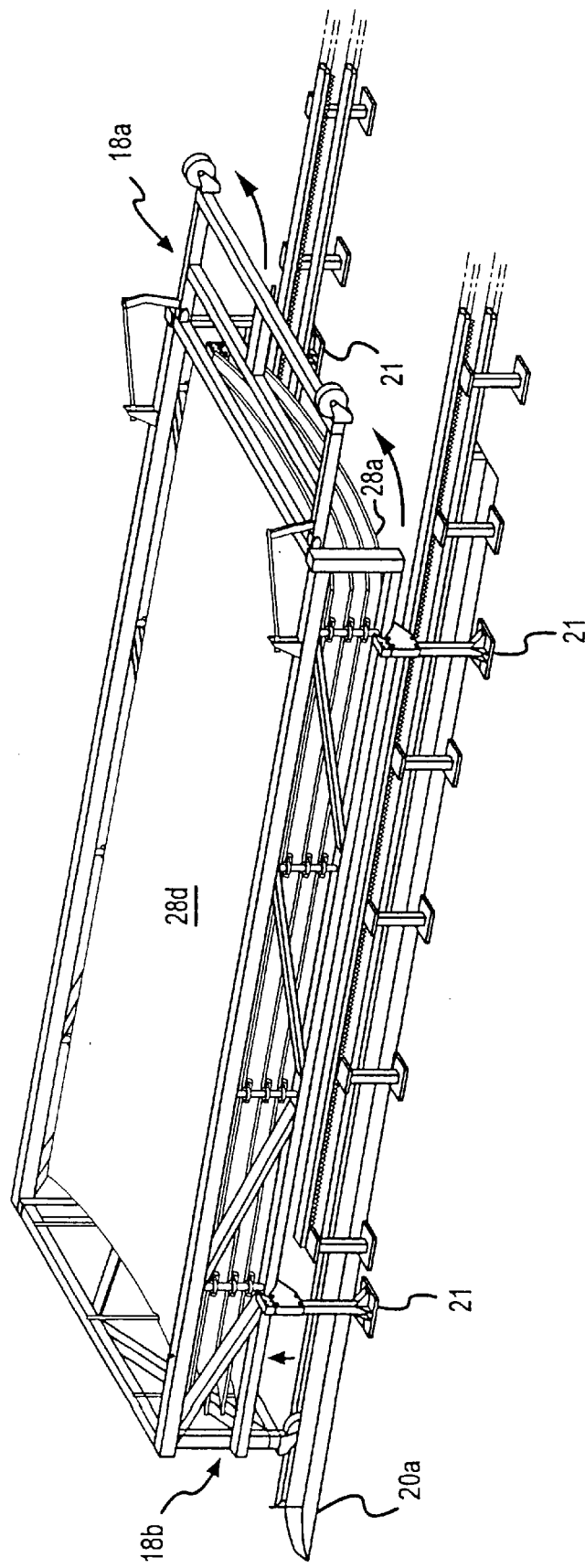
FIG. 3 is a perspective view of the plurality of panels supported by the panel transportation cart of the system illustrated in FIG. 1, the panel transportation cart being positioned at a lift location.
Figure 4:
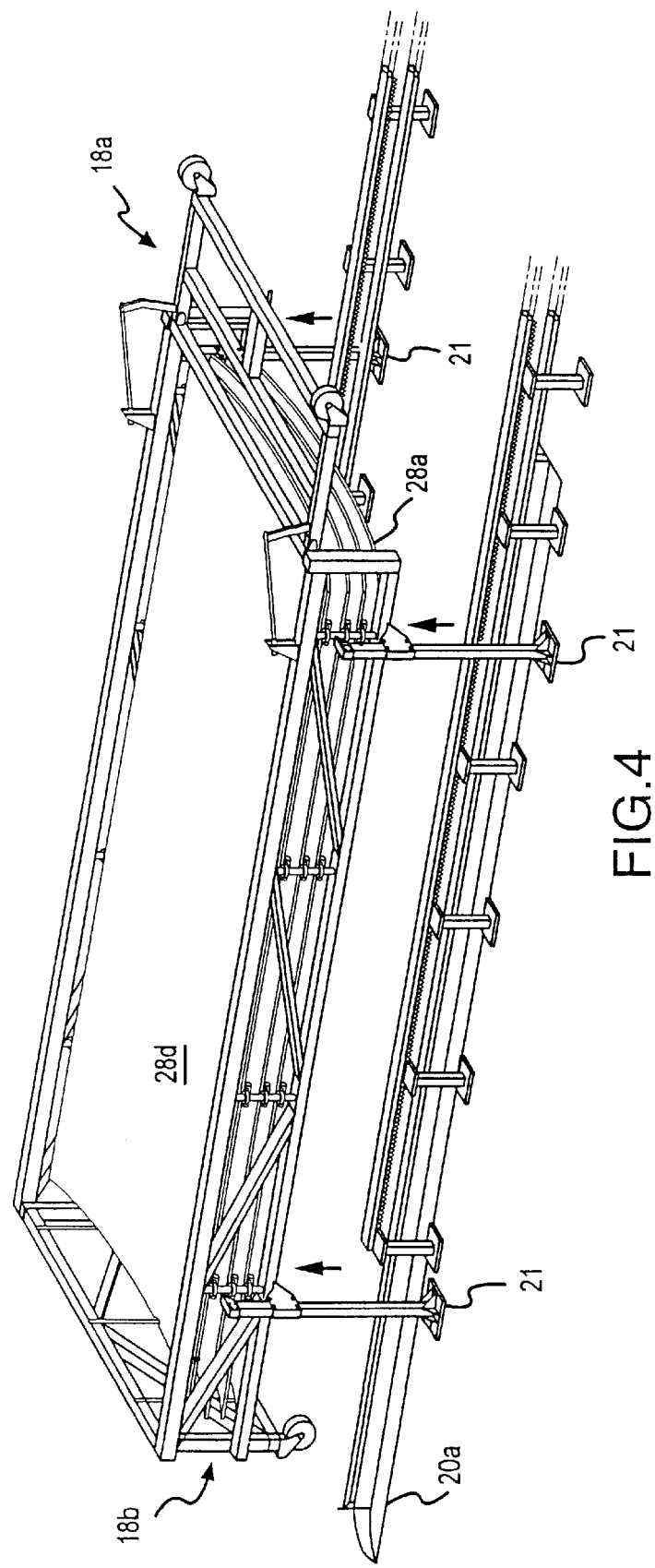
FIG. 4 is a perspective view of the plurality of panels supported by the panel transportation cart of the system illustrated in FIG. 1, the panel transportation cart being vertically moved by a lift system.
Figure 5A:
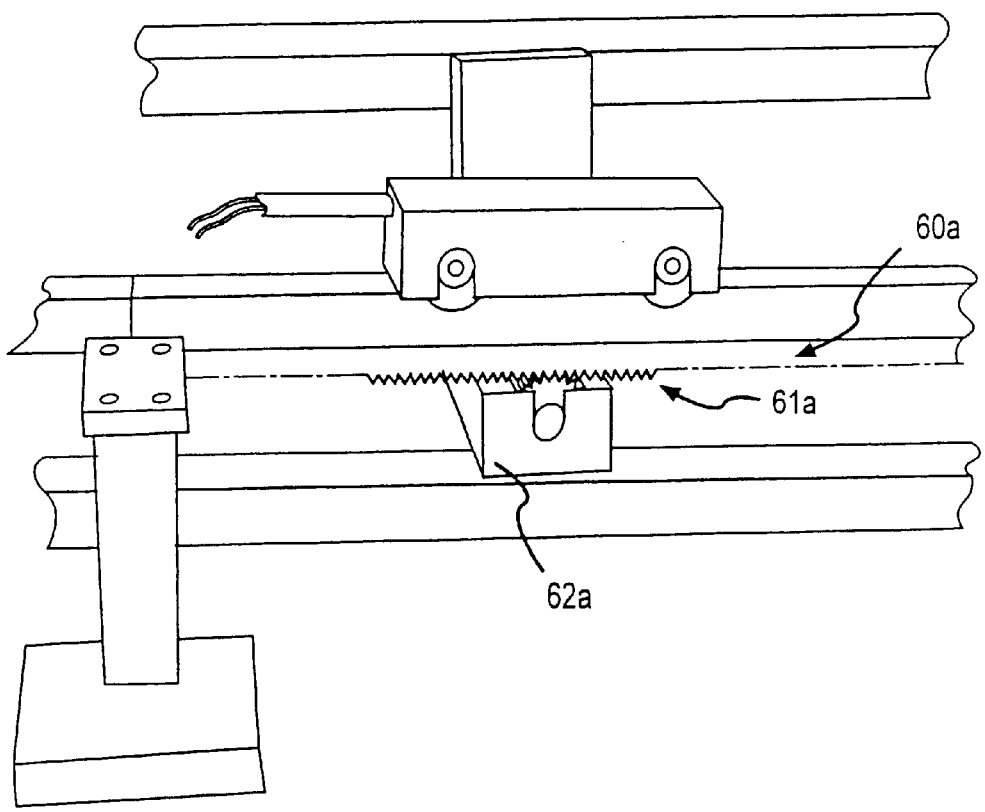
FIG. 5A is an enlarged view of the circled area indicated in FIG. 5.
Figure 5B:
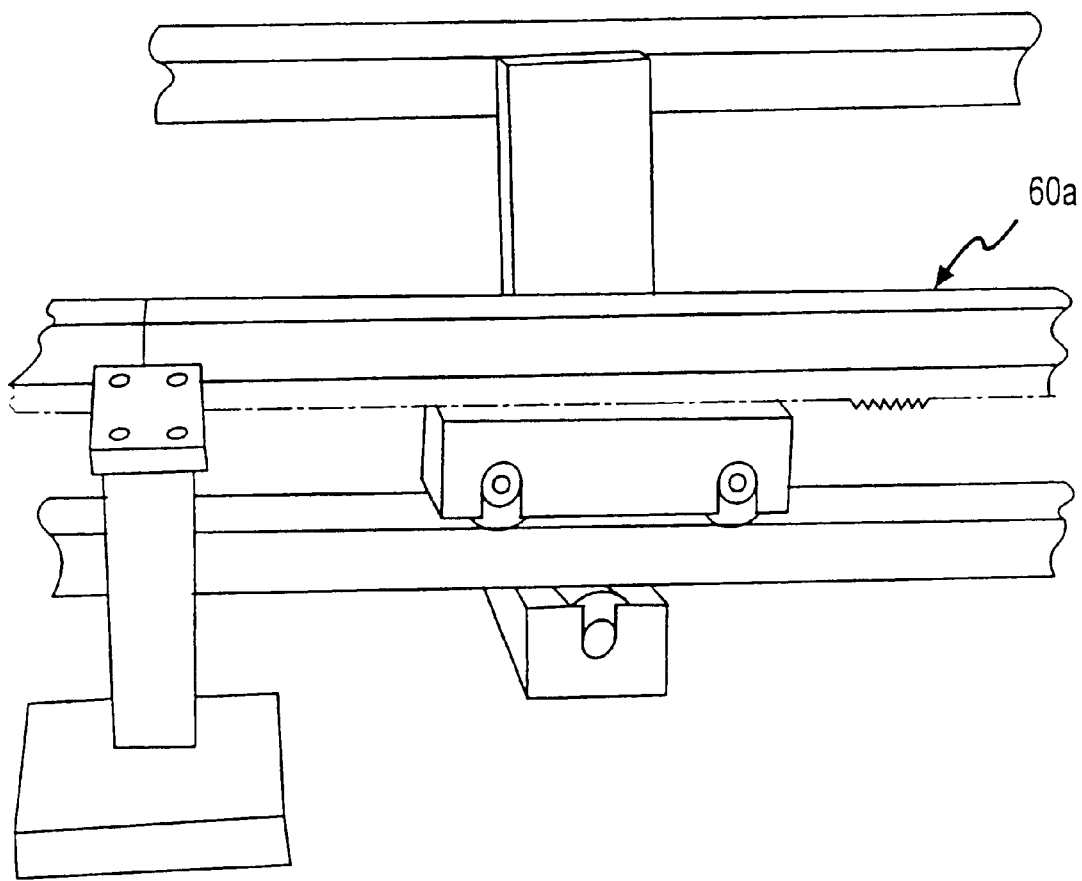
FIG. 5B is an enlarged view of the circled area indicated in FIG. 5.
Figure 6:
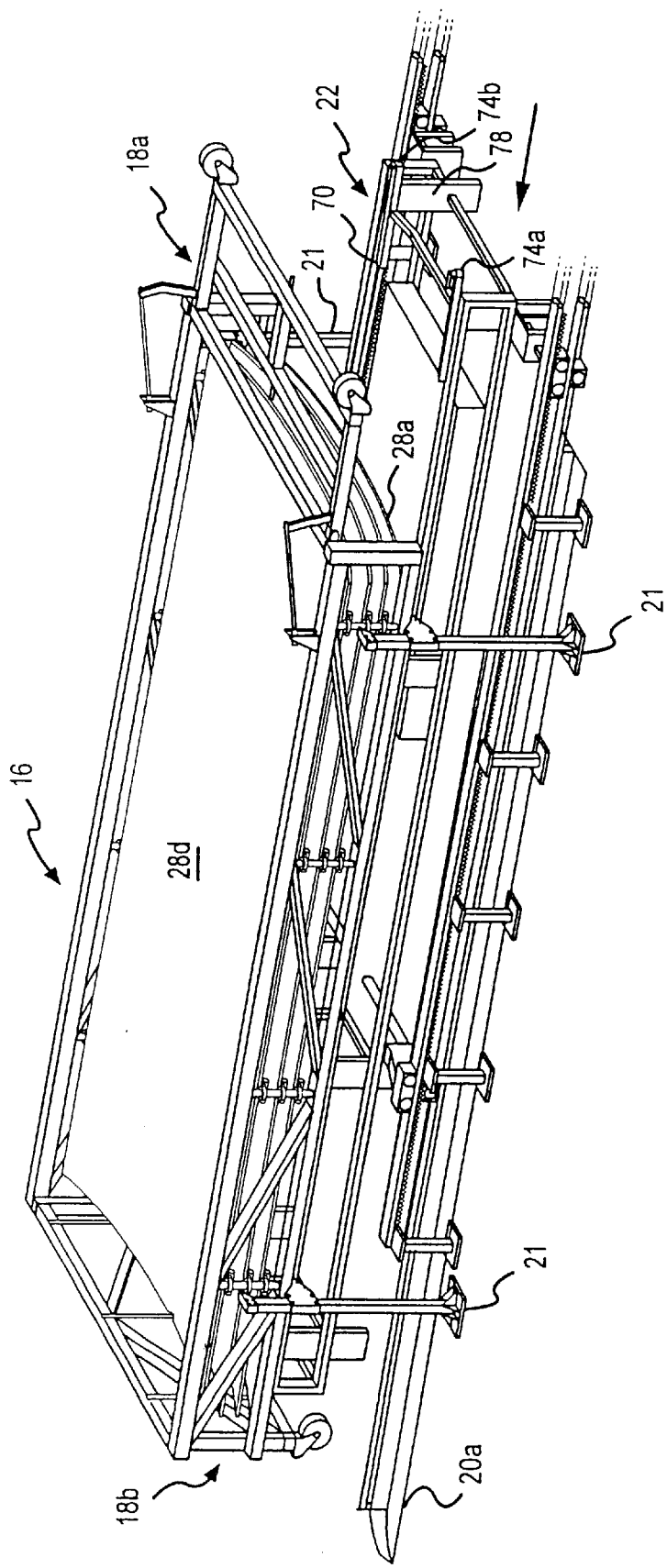
FIG. 6 is a perspective view of the panel position shuttle system being positioned beneath the panel transportation cart of the system illustrated in FIG. 1, to receive a first panel.

In particular, in referring to FIG. 2, the panel transfer cart 16 is configured to support a plurality of panels 28a–28d which, when cleaned and welded together, form a barrel suitable for use in a launch vehicle propulsion tank. In order to facilitate and enhance barrel processing efficiency, the panel transportation cart 16 includes first and second wheel assemblies 18a, 18b which allow for easy movement of the panels 28a–28d from a first location (e.g., an unloading area) to a second location (e.g., the panel transfer and processing area). Referring to FIGS. 1 and 3, once the panel transportation cart 16 arrives at the panel processing area, the panel transportation cart 16 may be guided into tracks 20a, 20b to ensure at least rough alignment of the panels 28a–28d with the panel positioning shuttle 22 and the weld preparation station 34. Once received within the tracks 20a, 20b, the panel transportation cart 16 is positionable about the lifts 21 which are capable of lifting the panel transportation cart 16 and panels 28a–28d supported thereby, such that the panel positioning shuttle 22 may be positioned thereunder to receive at least the first panel 28a. Furthermore, the first wheel assembly 18a is pivotable about the frame of the panel transportation cart 16 to allow passage of the panel positioning shuttle 22 thereunder to retrieve/receive one of the panels (e.g., the first panel 28a), as illustrated in FIGS. 3–4. In addition, the cart 16 includes at least a first alignment bar 23 which is receivable within slots 29 of the panels 28a–28d to ensure proper positioning (e.g., centered) of the panels on the shuttle 22 and alignment of the inner and outer edge wall portions 38a, 38b of the panels with the weld preparation station 34. A second alignment bar may also be included on the opposite end of the cart 16. In one embodiment, the first and second alignment bars have first and second different dimensions to ensure the panels are correctly oriented and positioned.

FIGS. 5–8 generally illustrate the features of the panel transportation cart 16 and panel positioning shuttle 22 which enable the panel positioning shuttle 22 to retrieve/receive at least the first panel 28a from the panel transportation cart 16. Generally, the lifts 21 function to adjust the vertical position of the panels relative to the shuttle 22 by vertically adjusting the position of the cart 16. Associated with the lifts 21 are servo drives which function to lower/raise the cart 16 such that the lower-most panel (e.g., the panel to be processed) is positioned at a selected height for retrieval by the shuttle 22. In this regard, the servo mechanism is commanded to go to one of four absolute positions. Each of these positions puts the belly of the next available panel at a common distance from the floor.

Figure 7:
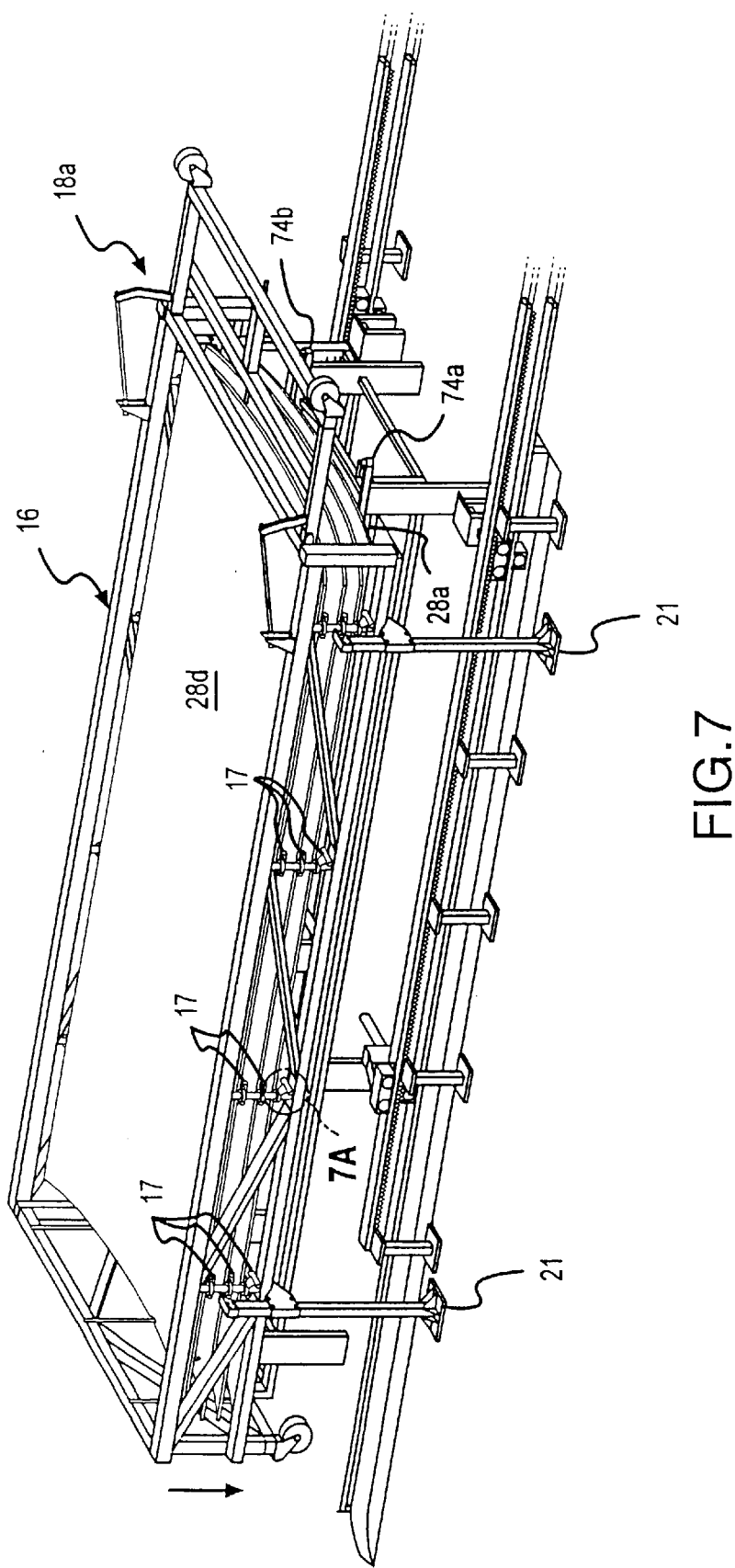
FIG. 7 is a perspective view of the panel position shuttle system positioned beneath the panel transportation cart of the system illustrated in FIG. 1, to receive the first panel.
Figure 7A:
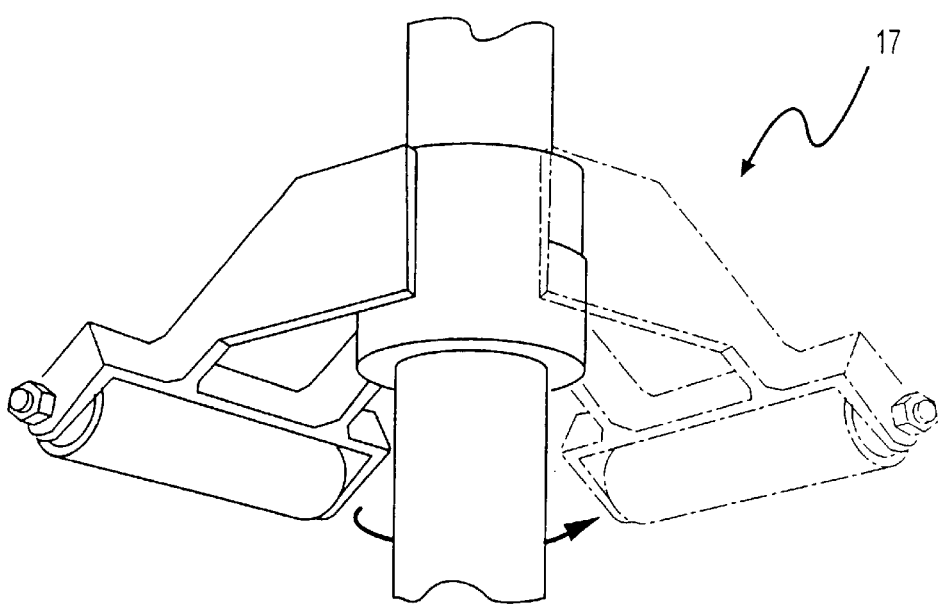
FIG. 7A is an enlarged view of the circled area indicated in FIG. 7.
Figure 8:
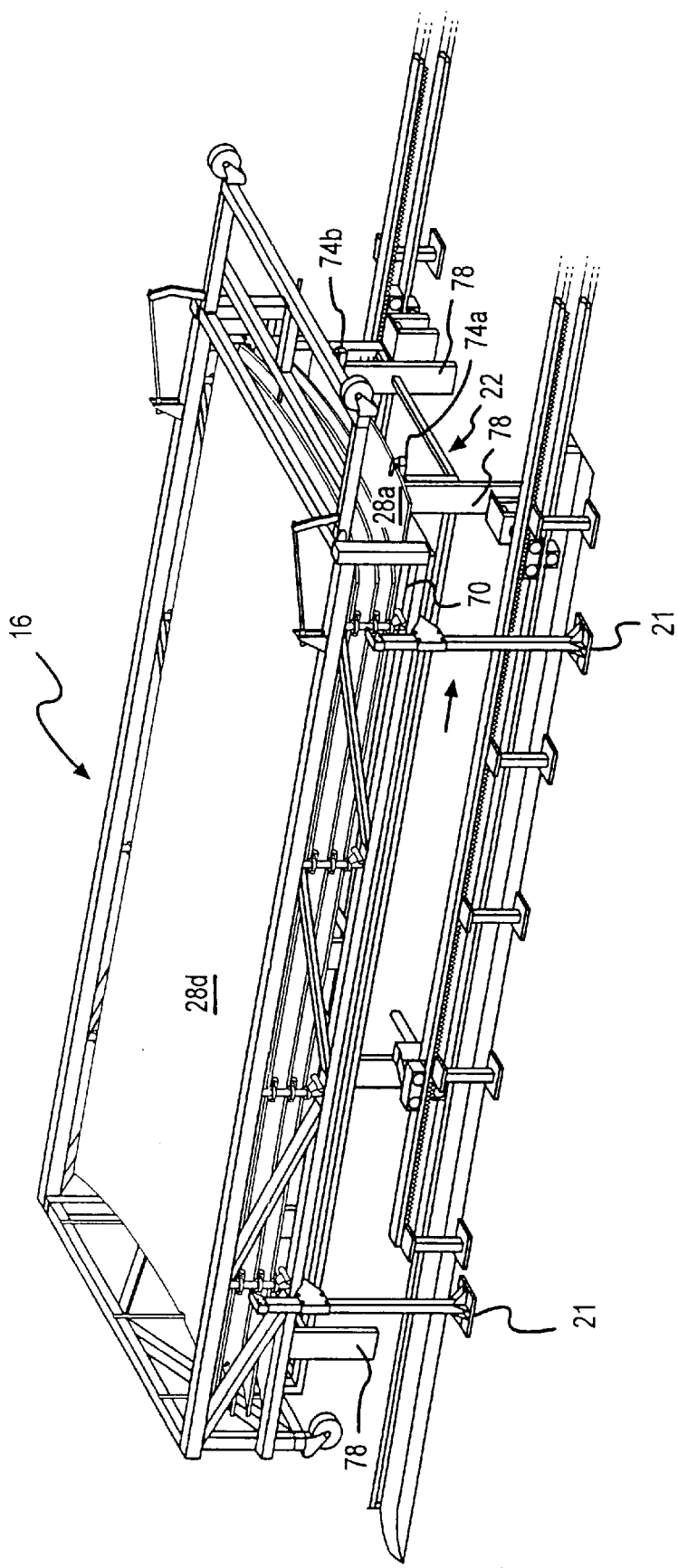
FIG. 8 is a perspective view of the first panel supported by the panel position shuttle system illustrated in FIG. 1.

In order to allow retrieval of the lower-most panel and transport the panel through the system for processing, the panel positioning shuttle 22 is movable along rails 60a, 60b via a drive system having a speed and torque controlled motor which drives the rear gears 62a, 62b, which interface with the gear racks 61a, 61b of the rails 60a, 60b, respectively. The drive system is capable of moving the shuttle 22 along the rails 60a, 60b to a position beneath the panel transportation cart 16 and is further capable of raising a carriage assembly 70 thereon to a raised position to retrieve/ receive and lower at least the first panel 28a from the panel transportation cart 16, and specifically, from swing-out rollers 17 which support the panels at various incremental heights. The shuttle 22 may include sensors (e.g., optical, contact, etc.) for slowing and stopping the shuttle 22 so that the first panel 28a may be received on the carriage or saddle assembly 70 at a selected position. FIG. 7A illustrates one embodiment of the swing-out rollers 17, the rollers being capable of rotating from a first position supporting a panel to at least a second position to allow the panels to be lowered onto the panel transportation cart 16. The lower-most panel 28a is located first, and the next lower swing-out roller 17 may be rotated to a support position whereupon the next panel 28b is lowered and so on. The aforementioned process is done manually at a remote cart-loading station and thereafter the swing-out rollers 17 are stationary.

Figure 9:
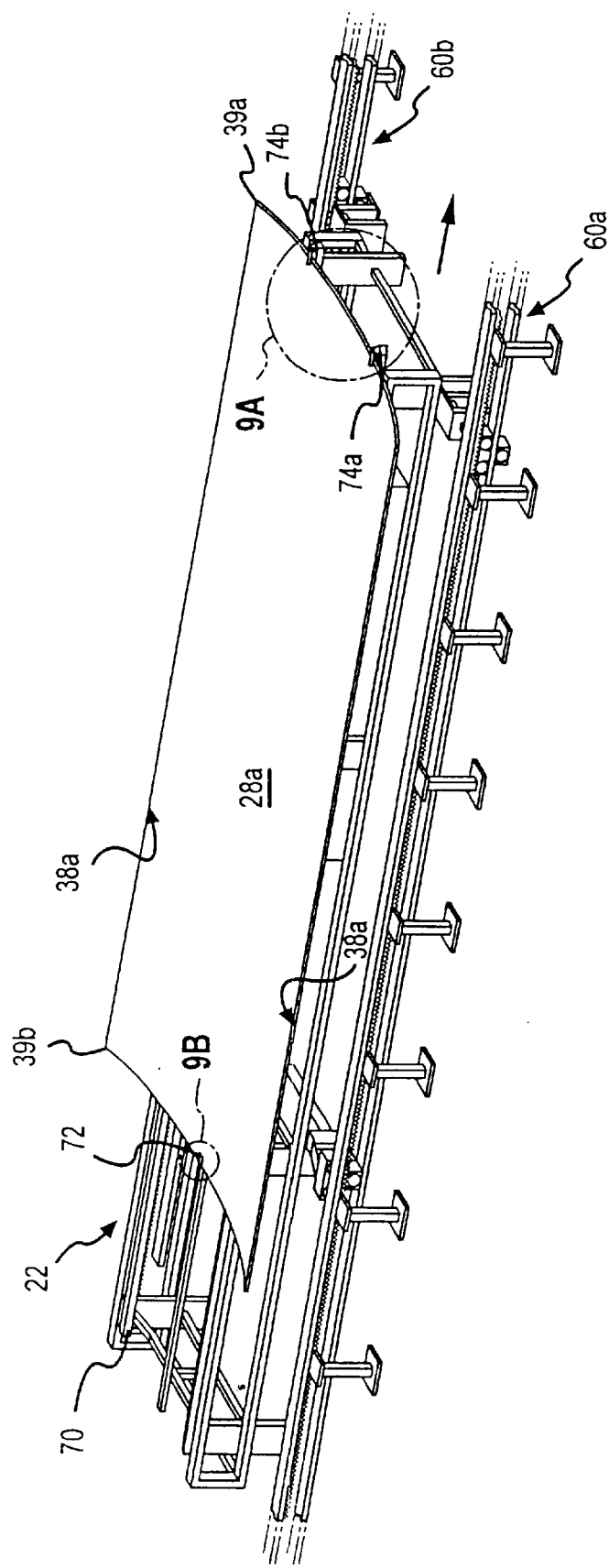
FIG. 9 is a perspective view of the first panel being transported by the panel shuttle system toward a panel weld preparation area illustrated in FIG. 1.
Figure 9B:
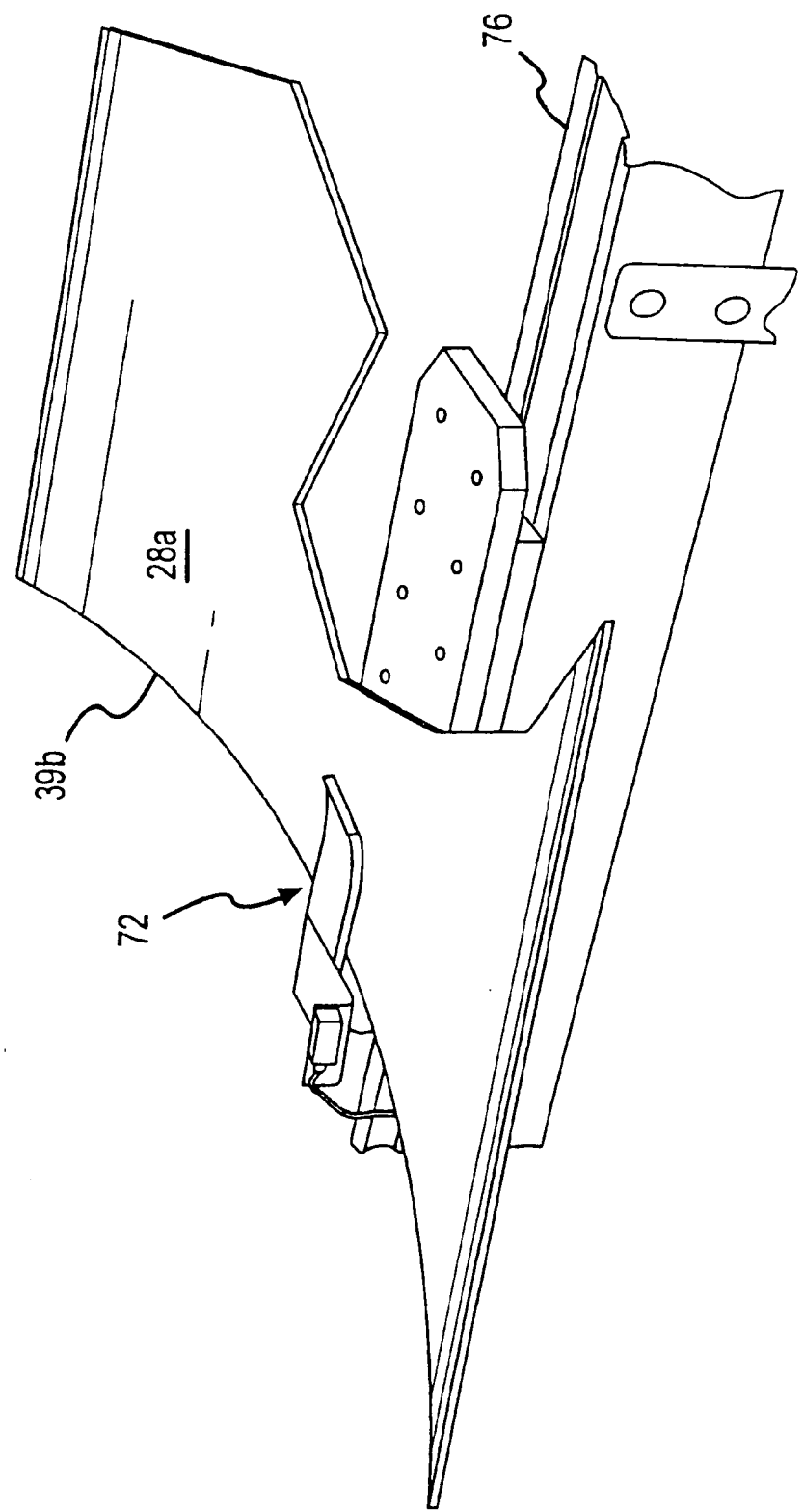
FIG. 9B is an enlarged view of the circled area indicated in FIG. 9.

Extraction of at least the first panel 28a is accomplished by first lifting the panel 28a off the rollers 17 (e.g., about 1 inch) and moving the first panel 28a via the shuttle 22 horizontally until the panel 28a is clear of the cart 16. Once the first panel 28a is received onto the carriage 70 of the panel position shuttle 22, the first panel 28a may be lowered to the appropriate height for preparation at the cleaning station 34. In order to secure the panel on the carriage 70, a plurality of translationally positionable clamps 72, 74a, 74b are provided on the panel position shuttle 22. In particular, and referring to FIGS. 9 and 9A, the clamps 74a, 74b are capable of translational movement in order to abuttingly engage the end wall 39a of the first panel 28a. The clamps 74a, 74b additionally function to support the weight of the first panel 28a when the panel is being positioned for placement upon the vertical weld assembly 50 (to be described in more detail hereinbelow). The panel clamps 74a, 74b are movable a discrete distance via timed feed rate to engage the aft end wall 39a. The panel position shuttle 22 also includes a single clamp 72 for engaging the fore or second end wall portion 39b to accommodate panels of varying lengths, the clamp 72 being movable along the rail 76 of the panel position shuttle 22. Additionally, the clamp 72 may also include a sensor (e.g., optical, contact) for determining when the clamp 72 engages the end wall portion 39b of the first panel 28a (e.g., to stop the clamp 72 upon engagement), as illustrated in FIGS. 9 and 9B. The clamp 72 also functions to support the panel 28a as the panel 28a is positioned onto the vertical weld fixture 50 and to confirm the centerline alignment of the saddles 70 of the shuttle 22.

Figure 10:
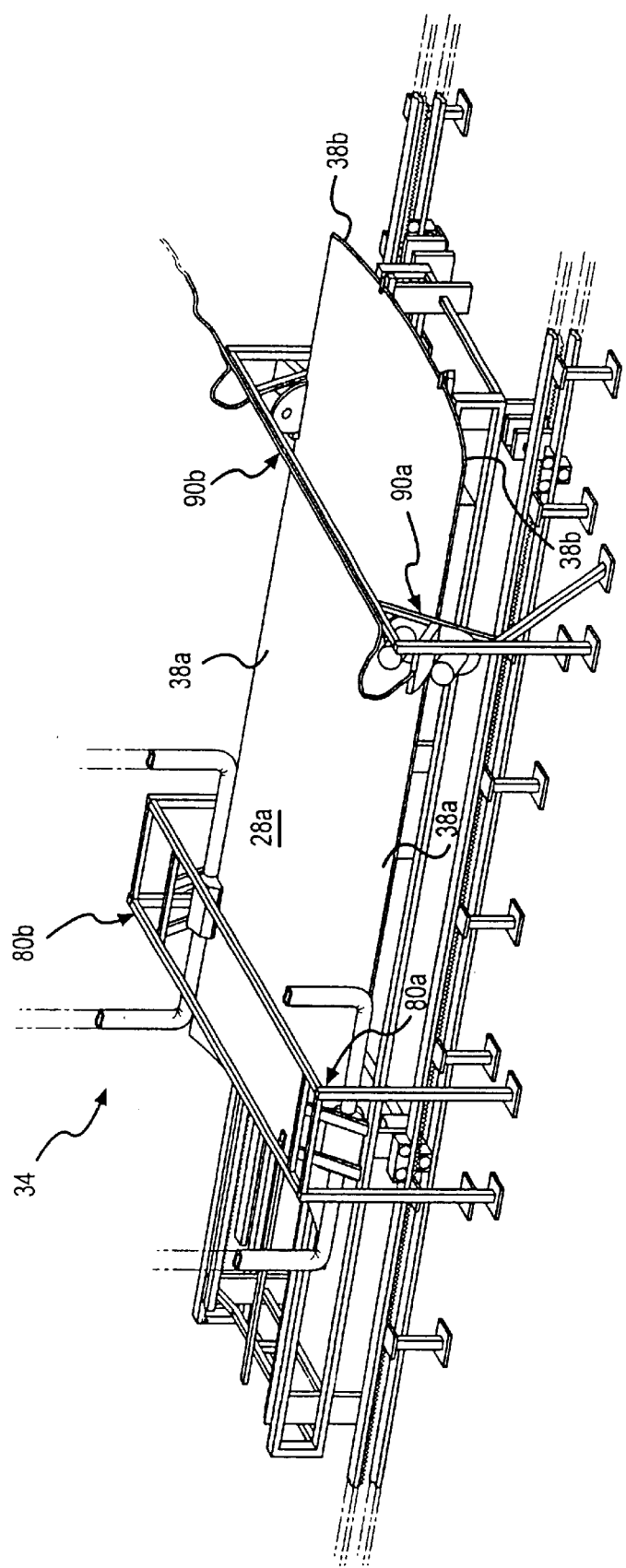
FIG. 10 is a perspective view of the weld preparation station illustrated in FIG. 1, showing the cleaning and sanding stations.

As noted in FIG. 10, the system 10 of the present invention further includes a weld preparation station 34, which includes a carbon dioxide ($CO_2$) system 80a, 80b for cleaning the inner and outer edge wall portions 38, 38b (i.e., weld lands) on both sides of the first panel 28a, and a sanding system 90a, 90b for sanding the inner and outer edge wall portions 38a, 38b of both sides of the panel 28a to remove at least 0.001 inch/side of material (e.g., aluminum oxide and aluminum) therefrom. Specifically, and referring to FIGS. 10A–10B, the carbon dioxide cleaning system 80a, 80b of the present invention functions to blast carbon dioxide pellets or granules against the inner and outer edge wall portions 38a, 38b on the side portions of the first panel 28a in order to clean or remove contaminants, such as oil, grease or other non-volatile residue and particulates (e.g., organics) from these edge wall portions 38a, 38b, which can adversely affect the weldability of the edge wall portions to similar portions of another panel (e.g., a second panel 28b). In the event such contaminants are not removed prior to sanding of the weld lands, there is a risk that the contaminants will be smeared into the panel during the sanding process, which, in turn, can degrade the weld integrity.

Figure 10A:
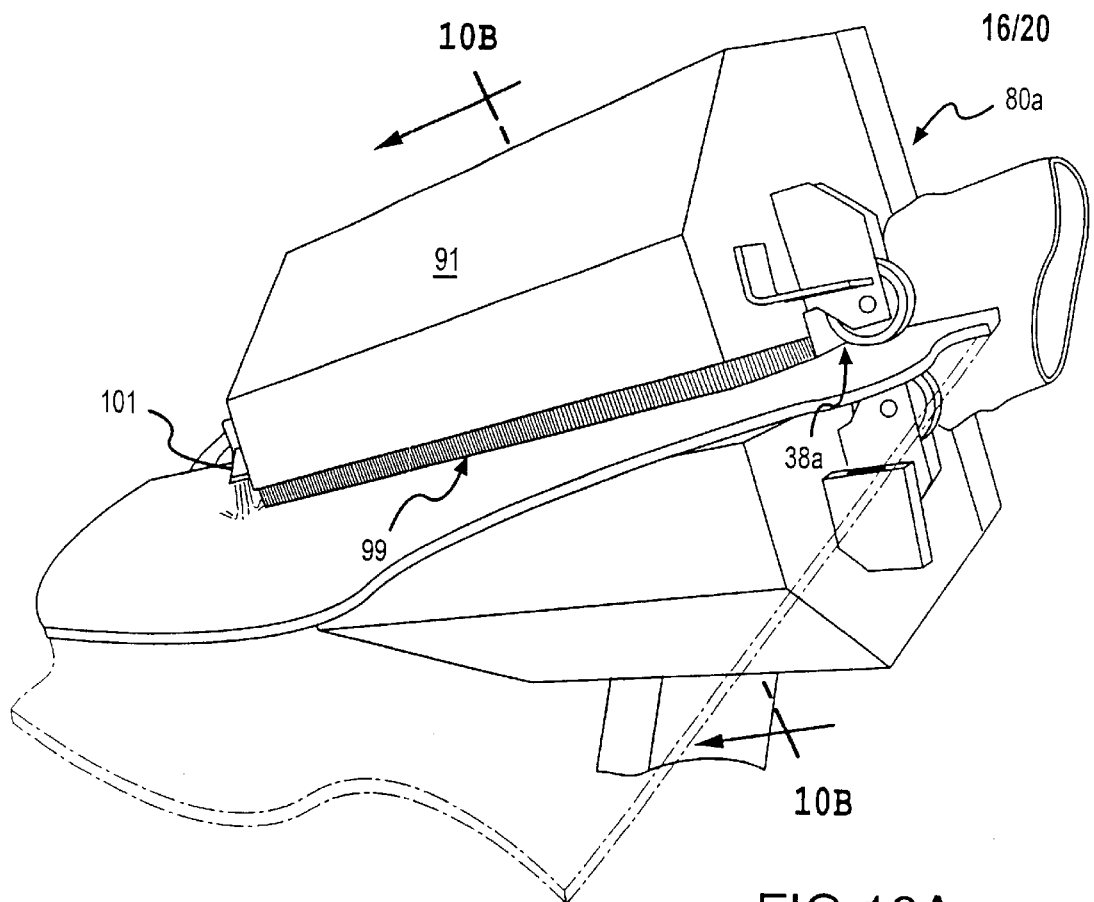
FIG. 10A is a perspective cut-away view of the cleaning station illustrated in FIG. 10.
Figure 10B:
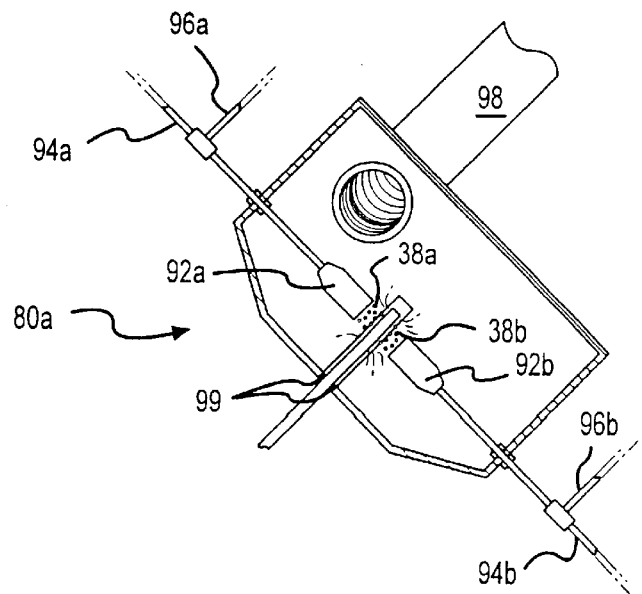
FIG. 10B is a cross-sectional view of the cleaning station illustrated in FIG. 10A, taken along line 10B—10B.

In one embodiment, illustrated in FIGS. 10A, 10B, the carbon dioxide cleaning system 80a, 80b each includes first and second nozzles 92a, 92b (e.g., venturi-type nozzles) for impacting a plurality of carbon dioxide pellets or granules suspended in a high velocity, filtered and heated air stream against the weld land area (e.g., inner and outer edge wall portions 38a, 38b on both sides of the panel 28a). Such nozzles 92a, 92b may be sized to have a width which corresponds to the width of the inner and outer edge wall portions 38a, 38b which need to be cleaned for welding (e.g., one inch width). In this embodiment, the carbon dioxide pellets generally have a dimension of about 0.080 inch. However, the size of such pellets may be varied in order to achieve more aggressive cleaning and/or removal of material. Of course, the velocity of the shuttle 22 supporting the panel 28a may be varied to enhance cleaning of the inner and outer edge wall portions 38b, 38b, and, in some instances, may be slowed to not only clean the inner and outer edge wall portions 38a, 38b, but also to remove at least 0.001 inch/side of material from the inner and outer edge wall portions 38a, 38b (e.g., to remove a layer of aluminum oxide) to enhance the weldability thereof.

The carbon dioxide pellets or granules are deliverable through a conduit 94a, 94b and are entrained in the heated, filtered and compressed air flow which is delivered via conduits 96a, 96b. In order to deliver the granules of carbon dioxide (e.g., dry ice) against the inner and outer edge wall portions 38a, 38b to achieve sufficient cleaning, the air delivered through conduits 96a, 96b is filtered and heated to a temperature of about 70° F. to about 150° F., depending upon the humidity level of the room in which the system is contained, and compressed to a pressure of about 100 psi, and, in a preferred embodiment, the filtered, compressed air is heated to a temperature of about 140° F. and it is compressed to about 100 psi. The panel 28a may be fed through the cleaning system 80a, 80b at a speed of about 18 inches/minute.

Since the carbon dioxide granules impact the inner and outer edge wall portions 38a, 38b on the sides of the panel 28a and sublimate to dissolve the greases and oils while blasting off the non-volatile residue and particulates, the carbon dioxide cleaning systems 80a, 80b also include a vent or exhaust system 98 (e.g., vacuum) for creating a negative pressure environment within the enclosure 91, and further includes wipers to inhibit leakage of carbon dioxide gas from within the enclosure 91 to the outside environment The exhaust system 98 thus functions to remove the resulting suspended particulates and to inhibit carbon dioxide gas from escaping into the surrounding environment, which could result in displacement of oxygen in the surrounding atmosphere. The carbon dioxide cleaning system 80a, 80b farther includes air knives 101 for blowing heated, filtered air against the inner and outer edge wall portions 38a, 38b to dry such portions after cleaning. As a result of this cleaning process, the weldability of panels to each other is enhanced due to reduced amounts of impurities (e.g., organic materials) thereon. In addition, the cleaning process of the present invention reduces cycle-time because it can be accomplished in parallel to the actual panel locating and welding for three of the four panels. Further, the cleaning process requires no actual touch labor.

Figure 10C:
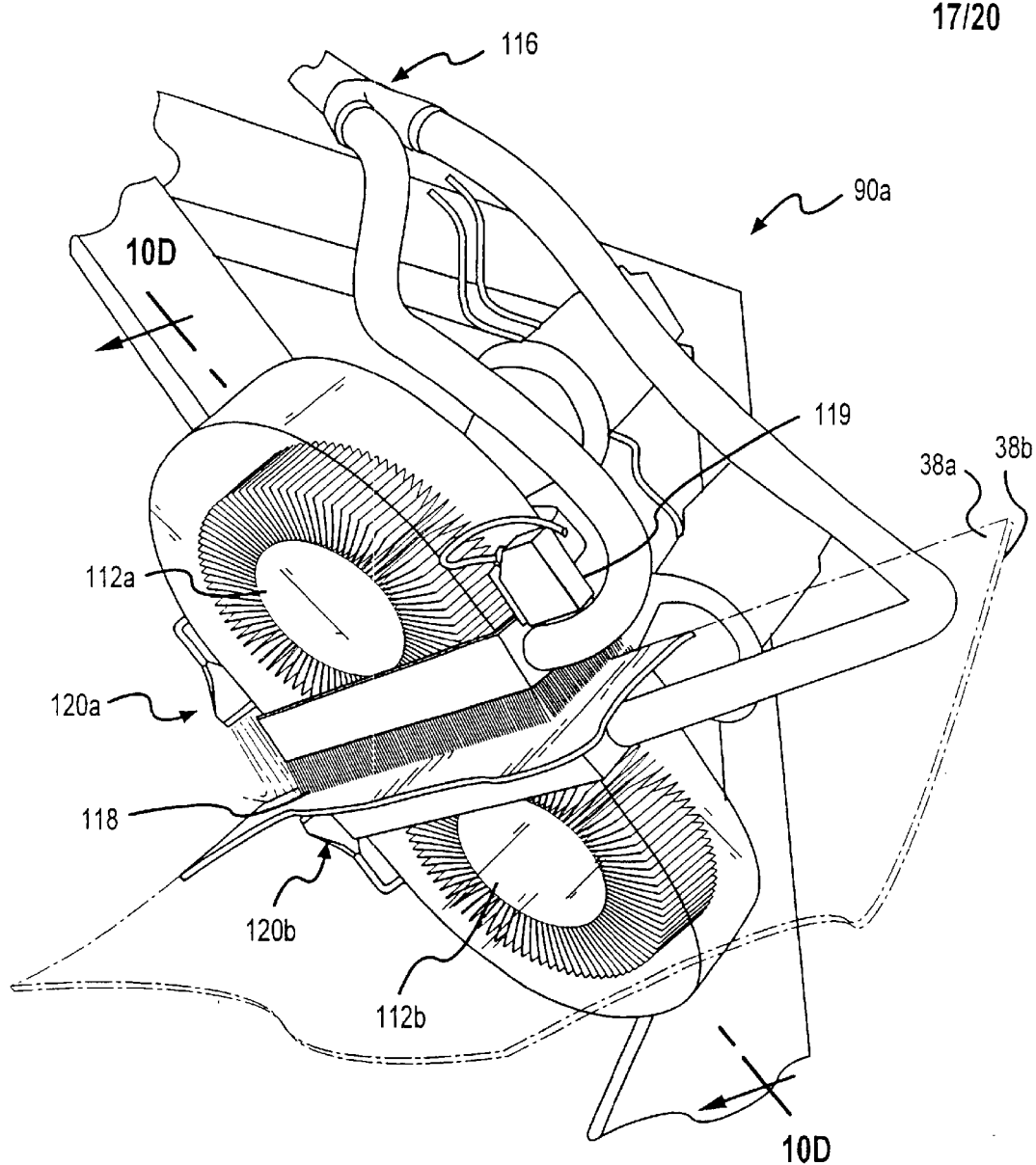
FIG. 10C is a perspective, cut-away view of the sanding station illustrated in FIG. 10.
Figure 10D:
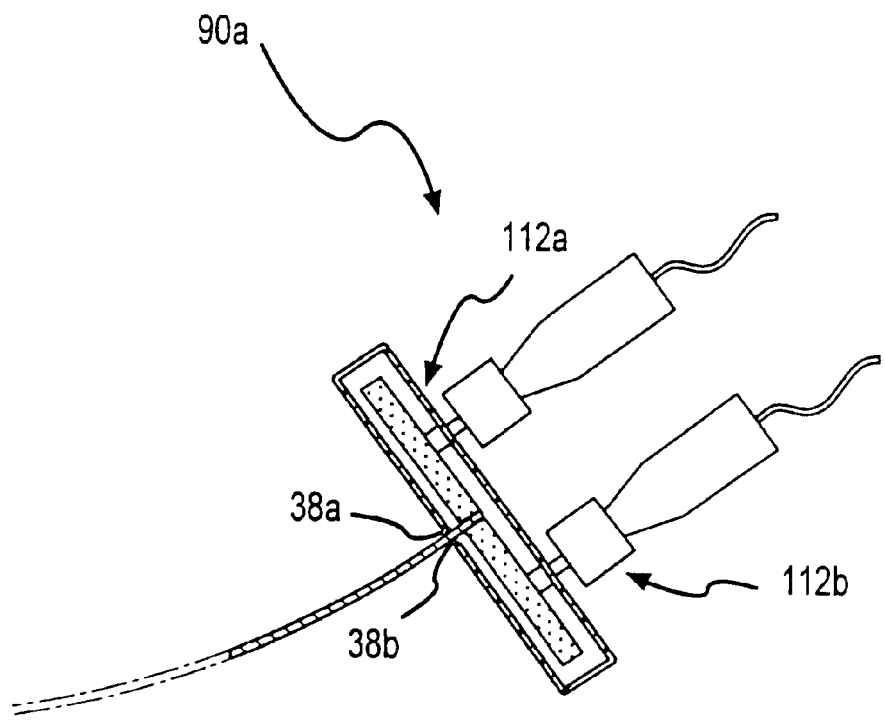
FIG. 10D is a cross-sectional view of the sanding station illustrated in FIG. 10C, taken along line 10D—10D.

Referring to FIGS. 10, 10C and 10D, the system 10 includes sanding systems 90a, 90b for sanding the inner and outer edge wall portions 38a, 39b on both sides of the panel 28a. More specifically, the sanding system 90a includes first and second sanding or flapper wheels 112a, 112b, which each include a plurality of sheets of sand paper having a grit of 120 or greater. Rotation of the sanding or flapper wheels 112a, 112b functions to remove at least about 0.001 inch layer comprising aluminum oxide and aluminum from the inner and outer edge wall portions 38a, 38b to further enhance the weldability of wall panels to each other. In order to remove a layer of between about 0.001 inch and about 0.003 inch from the inner and outer edge wall portions 38a, 38b on the sides of each panel 28a, the sanding or flapper wheels 112a, 112b are rotated such that the sheets of sand paper having a grit of 120 or greater have a surface speed across the inner and outer edge wall portions 38a, 38b of about 200,000 inches/minute. Further, the shuttle 22 may move the first panel 28a through the sanding system 90a at a velocity of about 18 inches per minute. Of course, the speed of the sheets of sand paper and/or the shuttle 22 may be varied, depending, among other things, the grit of the sand paper used, the material comprising the panel, and the amount of material to be removed from the inner and outer edge wall portions of the panel. The sander system 90a may further include a vacuum system 116 for removing sanding dust during sanding operations. A plurality of brushes 118 may be further included to engage the inner and outer walls of the panel 28a to reduce sanding dust escaping to the surrounding environment. The sanding system 90a may further include air knives 120a, 120b for blowing filtered, dried air to remove any excess dust remaining on the cleaned and sanded inner and outer edge wall portions 38a, 38b on both sides of the panel 28a. For purposes of sanding the inner and outer edge wall portions 38a, 38b of both sides of the panel 28a when such portions are appropriately positioned between the sanding wheels 112a, 112b for sanding operations, the sanding system 90a may also include a sensor 119 (e.g., infrared) which activates and deactivates the sanding wheels 112a, 112b.

Figure 11:
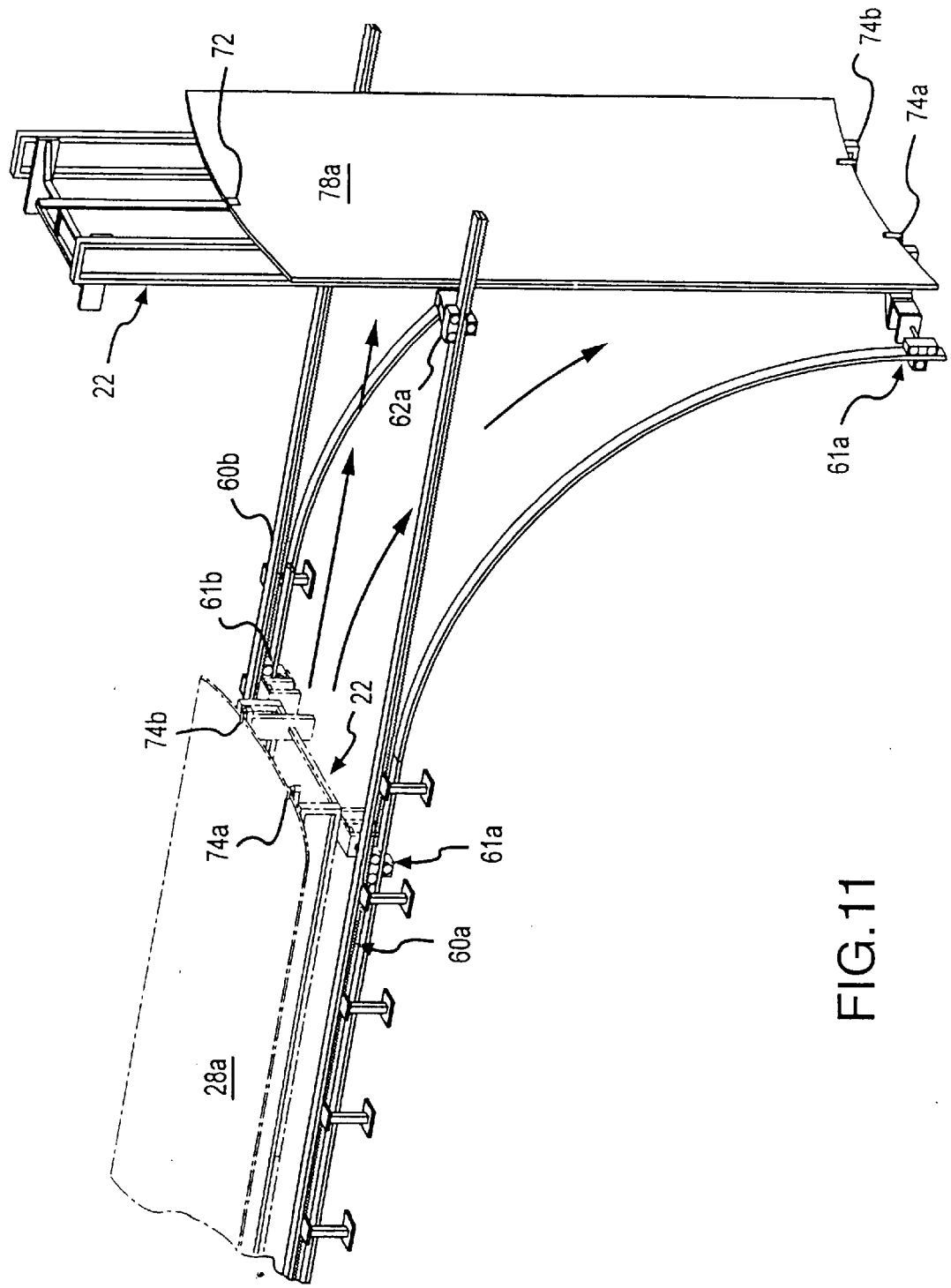
FIG. 11 is a perspective, progressive view of the panel position shuttle system transporting a panel toward a vertical weld structure illustrated in FIG. 1, from a horizontal to vertical orientation.
Figure 12:
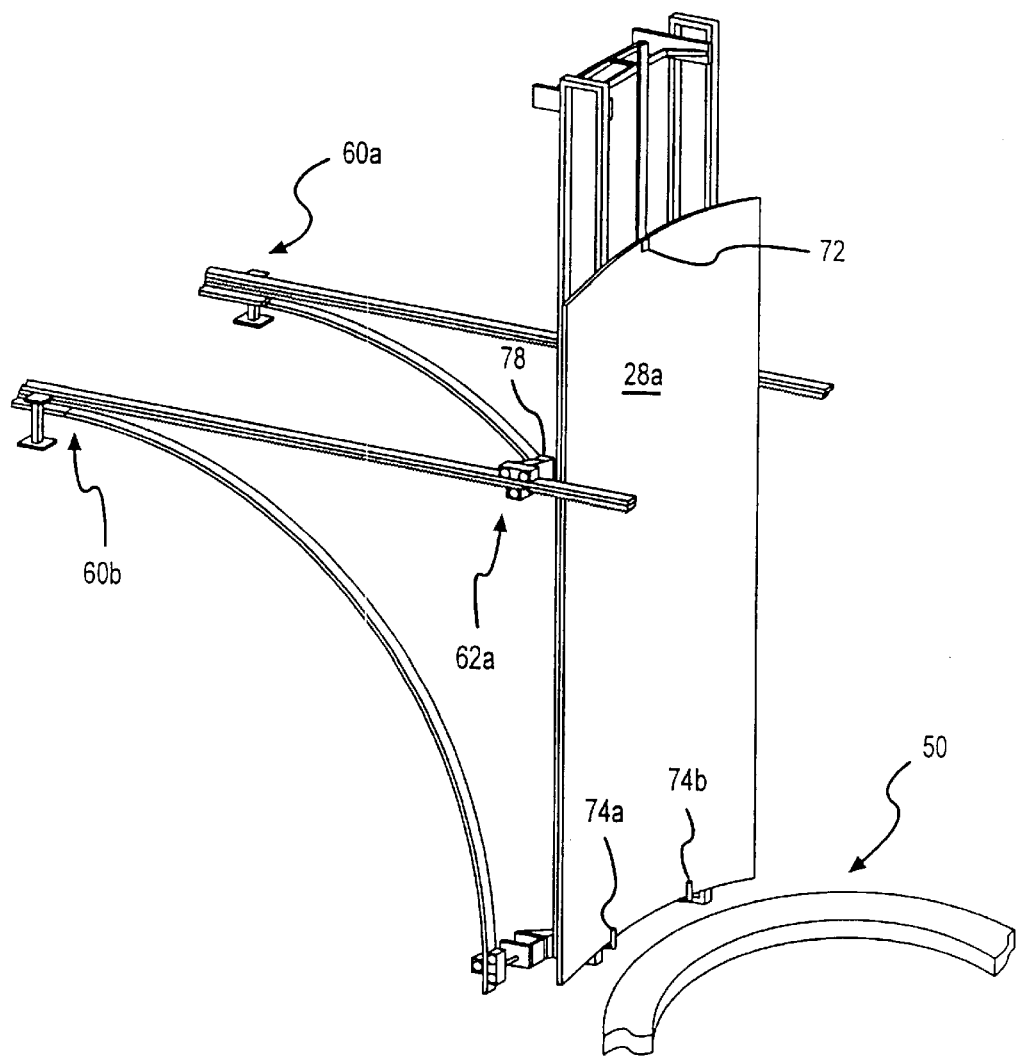
FIG. 12 is a perspective, cut-away view of a panel being positioned on the vertical weld structure illustrated in FIG. 1.

After the inner and outer edge wall portions 38a, 38b on each side of the panel 28a have been sanded, the shuttle 22 may then function to verticalize and position the panel 28a on the vertical weld fixture 50. More specifically, and referring to FIGS. 11–12, the motorized reels 62a, 62b of the shuttle 22 are engagable with gear rack 61a, 61b to generally drive and to govern the speed of the shuttle 22 as shuttle 22 moves along the tracks 60a, 60b from a horizontal to a vertical orientation. In one embodiment, the motors 62a, 62b go into a local jogging control mode as the panel 28a is verticalized. Thereafter, the lift mechanisms 78 utilized to raise the saddle/carriage assembly 70 to extract the panel 28 from the panel transportation cart 16 may be utilized to translate the panel 28a horizontally such that the panel 28a may be received upon rollers of the vertical weld fixture 50. Of note, the clamps 72, 74a, 74b function to hold the panel in a vertical position and during actuation to the vertical weld fixture 50.

Of note, the control station 150 of the system 10, illustrated in FIG. 1, controls the positioning and attendant functionality of the panel positioning shuttle 22 and may control operation of the weld preparation station 34. A second control station may also be provided in proximity to the vertical weld fixture 50 to allow monitoring and control of the system 10 therefrom.

The above-described system 10 may be further utilized for processing of panels 28b–28d. In this regard, a second panel 28b may be processed in accordance with the features of the present invention, and then positioned on the vertical weld fixture 50 adjacent to the first panel 28a for routing and welding to the first panel 28a. After such routing and welding, the resultant weld of the first and second panels may be inspected for defects in accordance with the digital x-ray inspection system of the present invention. Generally, the system includes a digital radiographic (non-film) system which uses a fiber optic scintillator (FOS) x-ray to light conversion screen coupled to a high resolution charged coupled device (CCD) camera to produce the radiographic images. The system eliminates some of the problems associated with radiographic images. In addition, the images from the system can be viewed immediately upon acquisition on a CRT monitor. Further, since the system is interconnected to the vertical weld machine, the barrel welds can be radiographically inspected immediately upon completion of the weld while the panels are still clamped in the vertical weld fixture.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method for handling panels, comprising the steps:

supporting each of a plurality of panels on a panel transportation cart in vertically spaced relation to define a stack of panels;

removing a lowermost panel from said stack of panels with said panel transportation cart being at a first location and while a remainder of said stack continues to be supported by said panel transportation cart, wherein said removing step comprises moving a panel shuttle in a first direction under said stack of panels on said panel transportation cart, raising a carriage of said panel shuttle into engagement with said lowermost panel on said panel transportation cart, terminating said supporting step in relation to said lowermost panel by said raising step, and moving said panel shuttle in a second direction after said raising step to remove said lowermost panel from said panel transportation cart;

processing said lowermost panel after said removing step and with said lowermost panel remaining on said panel shuttle; and transporting said lowermost panel from said first location to a second location on said panel shuttle.

2. A method, as claimed in claim 1, wherein:

said transporting step comprises moving said panel shuttle along a rail system.

3. A method, as claimed in claim 1, wherein:

each said panel in said stack of panels is disposed in a horizontal orientation on said panel transportation cart, wherein said removing step comprises maintaining said lowermost panel in a horizontal orientation.

4. A method, as claimed in claim 1, wherein:

said transporting step comprises changing an orientation of said lowermost panel.

5. A method, as claimed in claim 1, wherein:

said transporting step comprises changing said lowermost panel from a horizontal orientation at said first location to a vertical orientation at said second location.

6. A method, as claimed in claim 1, further comprising the steps of:

loading said plurality of panels on said panel transportation cart at a third location to define said stack of panels; and moving said panel transportation cart from said third location to said first location.

7. A method, as claimed in claim 1, further comprising the step of:

disposing said panel transportation cart on a pair of tracks at said first location, wherein said disposing step comprises aligning said stack of panels with said panel shuttle used by said removing and transporting steps.

8. a method, as claimed in claim 1, further comprising the step of:

pivoting a wheel assembly of said panel transportation cart at said first location, wherein said removing step is executed after said pivoting step.

9. A method, as claimed in claim 1, further comprising the step of:

lifting said panel transportation cart at said first location, wherein said removing step is executed after said lifting step.

10. A method, as claimed in claim 1, further comprising the step of:

loading said plurality of panels on said panel transportation cart, wherein said loading step comprises loading a first panel onto a first panel support of said panel transportation cart, moving a second panel support of said panel transportation cart into a panel supporting position after said loading a first panel step, and loading a second panel onto said second panel support after said moving a second panel support step, wherein said second panel is above said first panel in said stack of panels.

11. A method for handling panels, comprising the steps:

loading a plurality of panels on a panel transportation cart to define a stack of panels on said panel transportation cart, wherein said loading step comprises loading a first panel onto a first panel support of said panel transportation cart, moving a second panel support of said panel transportation cart into a panel supporting position after said loading a first panel step, and loading a second panel onto said second panel support after said moving a second panel support step, wherein said second panel is above said first panel on said panel transportation cart;

disposing said panel transportation cart at a first location;

removing a lowermost panel from said stack while said panel transportation cart is at said first location and while a remainder of said stack continues to be supported by said panel transportation cart; and transporting said lowermost panel from said first location to a second location.

12. A method, as claimed in claim 11, wherein:

said loading step is executed at a third location, wherein said method further comprises the step of moving said panel transportation cart from said third location to said first location for execution of said removing step.

13. A method, as claimed in claim 11, further comprising the step of:

disposing said panel transportation cart on a pair of tracks at said first location, wherein said disposing step comprises aligning said stack with a panel shuttle used by said removing and transporting steps.

14. A method, as claimed in claim 11, further comprising the step of:

pivoting a wheel assembly of said panel transportation cart at said first location, wherein said removing step is executed after said pivoting step.

15. A method, as claimed in claim 11, further comprising the step of:

lifting said panel transportation cart at said first location, wherein said removing step is executed after said lifting step.

16. A method, as claimed in claim 11, further comprising the step of:

supporting each of said plurality of panels on said panel transportation cart in vertically spaced relation to define said stack of panels, wherein said removing step comprises moving a panel shuttle in a first direction under said stack of panels on said panel transportation cart, raising a carriage of said panel shuttle into engagement with said lowermost panel on said panel transportation cart, terminating said supporting step in relation to said lowermost panel by said raising step, and moving said panel shuttle in a second direction after said raising step to remove said lowermost panel from said panel transportation cart.

17. A method, as claimed in claim 11, wherein:

each said panel in said stack is disposed in a horizontal orientation, wherein said removing step comprises maintaining said lowermost panel in a horizontal orientation.

18. A method, as claimed in claim 11, wherein:

said transporting step comprises moving a panel shuttle along a rail system.

19. A method, as claimed in claim 11, wherein:

said transporting step comprises changing an orientation of said lowermost panel.

20. A method, as claimed in claim 11, wherein:

said transporting step comprises changing said lowermost said panel from a horizontal orientation at said first location to a vertical orientation at said second location.

21. A method, as claimed in claim 11, wherein:

said removing step comprises disposing a panel shuttle under said stack and raising a carriage of said panel shuttle into engagement with said lowermost panel.

22. A method, as claimed in claim 21, wherein:

said transporting step comprises moving said panel shuttle along a rail system.

23. A method for handling panels, comprising the steps:

disposing a stack at a first location, wherein said stack comprises a plurality of panels, wherein said stack is disposed on a panel transportation cart;

removing a lowermost panel from said stack at said first location;

pivoting a wheel assembly of said panel transportation cart at said first location, wherein said removing step is executed after said pivoting step; and transporting said lowermost panel from said first location to a second location.

* * * * *